United States Patent
Stephens

(10) Patent No.: US 7,192,776 B2
(45) Date of Patent: Mar. 20, 2007

(54) SYNTHETIC URINE AND METHOD OF MANUFACTURING SAME

(76) Inventor: James Matthew Stephens, 550 Wards Corner Rd., Unit 102, Cincinnati, OH (US) 45140

( * ) Notice: Subject to any disclaimer, the term of this patent is extended or adjusted under 35 U.S.C. 154(b) by 0 days.

(21) Appl. No.: 10/766,165

(22) Filed: Jan. 28, 2004

(65) Prior Publication Data

US 2005/0164395 A1    Jul. 28, 2005

(51) Int. Cl.
*G01N 31/00*    (2006.01)

(52) U.S. Cl. .............................. 436/8; 436/18; 436/98; 252/408.1; 424/545

(58) Field of Classification Search .................... 436/8, 436/18, 98, 19; 252/408.1; 424/545
See application file for complete search history.

(56) References Cited

U.S. PATENT DOCUMENTS

| | | | |
|---|---|---|---|
| 3,880,646 A * | 4/1975 | Mc Connell et al. | 504/113 |
| 4,146,644 A | 3/1979 | Griffith et al. | |
| 4,714,564 A * | 12/1987 | Lynch et al. | 510/402 |
| 4,825,851 A * | 5/1989 | Cocks et al. | 601/4 |
| 4,989,607 A * | 2/1991 | Keusch et al. | 600/391 |
| 5,036,013 A | 7/1991 | Wood et al. | |
| 5,105,007 A * | 4/1992 | Adamczyk et al. | 562/450 |
| 5,176,668 A * | 1/1993 | Bernardin | 604/368 |
| 5,328,954 A | 7/1994 | Sarangapani | |
| 5,489,281 A | 2/1996 | Watanabe et al. | |
| 5,651,778 A * | 7/1997 | Melius et al. | 604/385.19 |
| 5,993,840 A * | 11/1999 | Fawkes et al. | 424/404 |
| 6,306,422 B1 | 10/2001 | Batich et al. | |
| 6,716,632 B1 * | 4/2004 | Dorn | 436/18 |
| 2002/0106807 A1 | 8/2002 | Novinski et al. | |
| 2004/0077106 A1 * | 4/2004 | Haddad | 436/536 |

\* cited by examiner

*Primary Examiner*—Maureen M. Wallenhorst
(74) *Attorney, Agent, or Firm*—McDonald Hopkins LLC

(57) ABSTRACT

A synthetic urine solution and method of its manufacture are disclosed. The solution includes water having a pH between 3 and 10. The solution further includes creatinine and means for removing bacteria from the solution so as to control or eliminate sepsis of the urine solution, preferably through the use of biocide. The solution exhibits a specific gravity of from 1.005 g/cm$^3$ to 1.025 g/cm$^3$. Additional compounds may also be included to further enhance the aesthetics or apparent authenticity of the synthetic urine produced according to this invention.

13 Claims, No Drawings

SYNTHETIC URINE AND METHOD OF MANUFACTURING SAME

BACKGROUND OF THE INVENTION

This invention relates to a composition and method of manufacturing synthetic urine.

The kidneys remove unwanted substances circulating in the blood by way of producing urine, which is excreted from the body. Consequently, diverse waste substances and other substances unwanted by the body find their way into urine for subsequent removal from the body. Urinalysis is the testing of the composition and amounts of waste substances in urine, and provides a tremendously powerful diagnostic tool for the medical profession. In particular, many of these substances are indicative of certain medical conditions or other substances which have been metabolized by a person's kidneys.

Using current urinalysis techniques, unwanted substances in a urine sample can mask existing medical conditions, while still some others can masquerade as non-existent medical conditions. In each instance, these unwanted substance undermine the usefulness of urinalysis as a medical diagnostic tool. Some of the unwanted substances that find their way into a urine sample are drugs (both legal and illegal) and metabolites thereof, along with other chemical residues or contaminants that may be present or otherwise contacted during the handling procedures. These substances can disturb the sensitive tests, making the actual state of the body difficult or impossible to determine.

For example, insulin levels, para-aminohippuric acid, phenol sulfonphthalein, phosphate, arylsulfatase-A, lysosome, urine amylase, total urine estrogens, specific estrogens, progestins, aldosterone, catecholamines, 5-hydroxyindoleacetic acid, cortisol, homovanillic acid, human chorionic gonadotrophin, creatine, urea, uric acid, bilirubin, hemoglobin, hydroxyproline, melanin, porphorins, total protein, acid mucopolysaccharide, copper, glucose oxidase and urine ketone can all influence the results of most standard urinalysis testing methods in unintended or unpredictable ways.

Essentially, these testing methods include a variety of immunoassays or assays by other techniques, such as isolation followed by gas or liquid chromatography followed by mass spectrometry. These tests make urinalysis a powerful diagnostic tool for identifying a whole range of conditions. For example, substance abuse and other indicia of disease or bodily state can easily be detected by urinalysis. However, in order to accurately establish standards of comparison for such tests, reliable urine samples are needed which are entirely free from any of the aforementioned substances. Thus, the development of a suitable, synthetic urine substitute would improve testing methods by providing researchers, potential urine donors and testing technicians with an accurate baseline reading for "clean" urine samples to compare against other suspect samples.

To illustrate, a method for detecting this compound is described in U.S. Pat. No. 5,036,013, issued to El Sohly et al., where various deuterated cannabinoids are synthesized to help determine the quantitative amount of tetrahydrocannabinol in a urine sample. One method in particular involves spiking a clean urine sample with known amount of deuterated tetrahydrocannabinol and analyzing the resultant sample with gas chromatography/mass spectrometry in order to establish set standards of comparison. However, a failure to possess a truly clean sample could substantially influence and negatively affect the results of these methods.

Another example of the problems created by interfering chemicals in urine is exemplified by the case of ibuprophan. Ibuprophan is a prostaglandin synthetase inhibitor that may be taken in large doses to relive pain and inflammation characteristic of arthritis. When a patient taking these massive doses is subjected to urinalysis, it may mask other drugs being taken by the donor, or may even be mistaken for tetrahydrocannabinol (a metabolite which many testing technicians classify as being indicative of marijuana use).

Any misidentification of controlled substance use/abuse, personal information (pregnancy, use of cigarettes, etc.) or any of the numerous medical conditions that can be determined using urinalysis can have devastating personal consequences for the urine donor. Thus, some companies sell inexpensive home testing kits in order to provide some level or reassurance to potential urine donors whether they may have such a misidentification. However, given the potential liability for a misidentified or positive test, many lay persons feel intimidated by testing procedures, and these persons would welcome the ability to utilize a known sample, free from unwanted or unknown substances, for the sake of comparison.

In response to the need for a reliable source of relatively inexpensive, "clean" urine samples which are free from any unwanted or unknown substances, numerous attempts to formulate synthetic urine have been made. For example, U.S. Pat. No. 6,306,422 to Batich et al. (table 3, col. 16, line 50 et seq.), U.S. Pat. No. 5,328,954 to Sarangapani (table 1, col. 9, line 29 et seq.), U.S. Pat. No. 5,489,281 to Watanabe et al. (col. 12, example 6) and U.S. Pat. No. 4,146,644 to Griffith et al. (table 1, col. 10). However, none of these references appears to address a simple composition which can be manufactured in an inexpensive manner.

Additionally, all of these references require the use of creatinine or other compounds which can be consumed by bacteria present in the sample. Accordingly, all of these samples will undergo sepsis unless they are immediately used, thereby making these compounds as unattractive candidates for mass production and/or consumer sales.

SUMMARY OF THE INVENTION

It is an object of this invention to provide a reliable source of synthetic urine, along with a method for its manufacture, which is free from any and all unwanted or unknown substances.

It is a further object of this invention to provide a synthetic urine, along with a method for its manufacture, which is capable of retaining its viability and utility for extended periods of time.

Still further uses for such a synthetic urine can and will be devised by a prospective user based upon her or her own personal disposition, interests and privacy concerns.

Accordingly, a composition of synthetic urine is claimed. This composition includes water, having a pH between 3 and 10 with creatinine and biocide dissolved therein. The composition further includes any compound which dissolves and dissociates in a water solution in a manner which insures that the specific gravity of the resulting solution mixture is between 1.005 $g/cm^3$ and 1.025 $g/cm^3$. Urea can be added as another possible element of the invention, and those skilled in the art will readily identify appropriate specific types of biocide oxiders, organics or in situ agents, along with a host of carbonates, halide salts, hydroxide salts and other chemicals which could serve as ideal ionic compounds within the meaning of the invention.

A method for manufacturing synthetic urine is also disclosed. The method involves providing water, dissolving creatinine and biocide in the water, adjusting the resulting solution's specific gravity to be between 1.005 and 1.025 and, if necessary, the pH level of the solution. In another aspect, the method contemplates providing water with a pH between 3 and 10, mixing creatinine and at least one dissociating ionic compound to adjust the specific gravity of the resulting solution to be between 1.005 g/cm$^3$ and 1.025 g/cm$^3$ and removing bacteria from the solution so as to avoid sepsis of the creatinine. In each of these embodiments the same types of biocides and ionic compounds can be used as were identified in the composition embodiment above.

DETAILED DESCRIPTION OF THE PREFERRED EMBODIMENTS

While human urine may at varying times reflect a wide range of chemical compounds, almost all current urinalysis rely upon observation of three basic traits: pH level, specific gravity and the presence of creatinine. Consequently, it was discovered that an effective, yet cost efficient, synthetic urine solution having a final specific gravity between 1.005 g/cm$^3$ and 1.025 g/cm$^3$ needed only to contain three basic components: water with a pH between 3 and 10; creatinine; and some means for controlling or eliminating the unwanted sepsis of the creatinine. With respect to this final element, this bacteria control/elimination is most readily accomplished through the use of a biocide.

Examining each of these three traits separately, the need for a water-based solution should be apparent. However, it is significant to note that human urine displays a wide range in terms of pH variation—anywhere from 3 to 10. This variation can be attributed to any number of factors regarding regional water quality, metabolic idiosyncrasies displayed by each individual and the like. Thus, the water supplied for the composition and method may need to have its pH adjusted accordingly. Significantly, while use of distilled, deionized water will produce the most reliable synthetic urine solutions in terms of elimination of unwanted substances, the invention may be practiced with equal efficacy using distilled water, deionized water or even regular tap water (drawn from any fresh water source having an appropriately low specific gravity—discussed below). Unless specifically noted to the contrary, use of the term "water" throughout this specification and appended claims is intended to embrace the broadest array of appropriate water sources available.

The final synthetic urine solution must also have a specific gravity between 1.005 g/cm$^3$ and 1.025 g/cm$^3$. Insofar as specific gravity is a measure of relative ionic content of a solution, it should be a apparent to those familiar with body chemistry or kidney functioning that certain ions and compounds will be commonly found in human urine, especially those commonly encountered in food and water sources (for example, sodium, potassium, chloride, etc.). In contrast, other elements will be inherently unwise choices at anything beyond a trace level (for example Lanthanoid and Actinoid series ions). The precise amount of the particular compound or compounds selected to adjust the specific gravity will depend directly on the concentration of compound (if in solution), the molecular weight of its constituents, water temperature, relative volume of water solvent being used and other similar factors. With respect to the water used to manufacture the synthetic urine of the present invention, it is anticipated that significant increases will need to be made to the specific gravity, as distilled, deionized water has a specific gravity of 1.000 g/cm$^3$ and tap water, while likely to vary by region, has a specific gravity around 1.003 g/cm$^3$.

In terms of the best compounds to utilize in adjusting the specific gravity, the single most important trait is that the compound must dissociate when dissolved in water. Additionally, it is preferred to find an inexpensive, widely available compound so as to minimize production costs. To that end, it is believed that carbonate salts, halide salts, hydroxide salts and certain bromides will have particular applicability. By way of illustration rather than limitation, these salts might include sodium bicarbonate, sodium, potassium, magnesium or calcium chlorides; sodium, potassium, or calcium hydroxides; and other similarly inexpensive and widely available salts.

Creatinine is a protein created in connection with muscular activity. As such, medical science recognizes creatinine as an important constituent in the human bloodstream and, to the extent that the kidneys cleanse and purify the bloodstream, in the waste stream expelled from the kidneys in the form of urine. Significantly, because creatinine is a protein, it is the subject of sepsis and decomposition. Thus, creatinine serves as an excellent indicator in urinalysis because it is indicative of human origin and, by virtue of its septic disposition, creatinine also provides a natural measure to determine whether or not a sample was, in fact, recently produced.

In order to insure stable creatinine levels in synthetic urine, it is therefore essential to remove or control the presence of sepsis-causing bacteria. However, whatever method of control is applied must also not interfere with the processes underpinning most urinalysis techniques. Thus, the use of an appropriate biocide is absolutely critical to the proper practice of the present invention. To the extent that human urine is sterile when excreted (under normal body conditions), the use of biocide represents a distinct departure from previous approaches to the manufacture of synthetic urine which relied solely on mimicking the compounds in actual urine without any regard for the long term shelf life of the synthetic solution. Moreover, it further demonstrates the need to select a biocide which is biologically active, yet does not interfere overtly with the chemistry of the synthetic urine solution itself (either through its chemical signature or by virtue of an abnormally large amount being detectable in the solution).

Biocide can be generically defined as substances used to control or eliminate microbial populations in a sample. Three general classes have been identified as having particular applicability when used in connection with the present invention: oxidizing biocides, organic biocides and a somewhat more generalized category referred to as in situ agents. Each will be discussed briefly below, although it should be understood that biocides are a term of art, known to those familiar with water chemistry processes.

Oxidizing biocides are generally self explanatory. This class includes any biologically effective agent which relies upon an oxidation process, including but not limited to various peroxides, hypochlorites, bromides and super oxides. Organic biocides encompass an expansive list of proteins and cyclical compounds known to those skilled in the art. In situ agents can be chemical compounds or actual physical processes designed to kill bacteria in a manner which is either self-generating or effective enough to prevent future degradation of the urine. Generic examples of such in situ agents include ozone, chlorine dioxide (or other dioxides), and ultraviolet radiation or irradiation processes followed by hermetic sealing of the sample.

Specific examples of various biocides contemplated above include: BHAP (such as 2-Bromo-4-hydroxyacetophenone, an organo-bromine group); Bronopol (such as 2-Bromo-2-nitropropane-1,3 diol, an organo-bromine group); Carbamates (such as a mix of sodium dimethyldithiocarbamate (DIBAM) and disodium ethylene bis-dithiocarbamate (NIBAM), or single product, such as potassium n-hydroxymethyl-n-methyldithiocarbamate, an organo-sulfur group); Chlorothioether (such as 2,2 Dihydroxy-5,5-dichlorodiphenyl monosulfide, a chlorinated phenolic thioether); DBNPA (such as 2-2-Dibromo-3-nitrilopropionamide, an organo-bromine group); DTEA, DTEA II (such as 2-(Decylthio)ethanamine, an alkylthioamine group); Guanides (including Guanidine and Biguanides) (such as dodecylguanidine hydrochloride and acetate, also polyhexamethylene biguanide hydrochloride, and tetradecylguanidine, all aliphatic guanadines); Glutaraldehyde (such as Pentane-1,5-dial., an aldehyde group); Isothiazolines (such as Alkyl isothiazolin-3-ones, an organo-sulfur group); MBT (such as Methylene bis(thiocyanate), an organo-sulfur group); Polyquat (such as broad-spectrum, cationic polymers of low molecular weight); Quats (ADBACs) (such as Alkyldimethylbenzylammonium chloride (also known as alkylbenzyldimethyl ammonium chloride or benzalkonium chloride), a quaternary ammonium compound group); Sulfone (such as Bis(trichloromethyl)sulfone, an organo-sulfur group); TBTO (such as Bis(tributyltin) oxide, an organo-tin group); TBZ (Tertbuthylazine) (such as 2-(tert-butylamino)-4-chloro-6-(ethylamino)-s-triazine, a Triazine group); TCCBN (such as Tetrachloro-2,4,6-cyano-3-benzonitrile, TCCBN functions similarly to the chlorophenols); TCMTB (such as 2(thiocyanomethylthio)benzothiazole); Thione (such as Tetrahydro-3,5,dimethyl-2H-1,3,5-thiadiazine-2-thione, an organo-sulfur group); THPS (TKHPS) (such as Tetrakish(hydroxymethyl)phosphonium sulfate, an alkyl phosphonium group); and TTPC (such as Tributyltetradecylphosphonium chloride, an alkylphosphonium group). Additionally, with respect to more commonly understood items, such as peroxides, hypochlorites and the like, it should be understood that this specification encompasses all forms of such compounds (for example, hydrogen peroxide, sodium peroxide, sodium hypochlorite, potassium hypochlorite, etc.). Other examples of biocides may exist and are expressly encompassed within the purvey of this specification.

Notably, as embraced by this specification, oxidizing biocides—and hypochlorite in particular—should not be confused with the agents that are employed to oxidize metabolites in urine samples. Such metabolite oxidizers are often referred to as "adulterants" within the urinalysis industry. Adulterants are substances deliberately added to actual urine samples to chemically alter the metabolites indicative of certain conditions so as to render these metabolites undetectable by standard urinalysis techniques.

Even though some substances like hypochlorite may possess utility as both a biocide and as an adulterant, the intended use of that substance (as either a biocide or an metabolite oxidizer) will substantially influence the conditions, concentration and manner in which the substance is provided. In particular, use as a biocide requires smaller concentrations and little to no regard for when the biocide is added during the manufacturing process. To illustrate, an oxidizing biocide such as sodium hypochlorite can be added in amounts as small as 1 mL per 3.8 L of water. Similar concentrations of other oxidizing biocides will have equal efficacy, as recognized by those skilled in the art.

In contrast, use of hypochlorite as an adulterant as taught, inter alia, in U.S. patent application Ser. No. 2002/0106807 must occur at higher concentrations and in a specific manner so as to oxidize certain metabolites or compounds. Thus, hypochlorite (and other oxidizing biocides) found in the present solution prevents the unwanted growth of bacteria. Moreover, to the extent that adulterants are often added to actual urine samples, the composition of the resulting mixture is substantially more complex, in terms of the variety of chemical species present, than the simplified composition of the present invention.

Another aspect of the present urine solution relates to the addition of urea in some form to the synthetic urine sample. While urea is not presently accounted for in most urinalysis techniques, its presence within a synthetic urine could add an additional level of realism for some applications. Notably, to the extent that urea is provided, it will need to be considered in the calculations of the amount of ionic dissociating compounds required to adjust the specific gravity and/or pH to the desired levels.

Other functionally inconsequential additives or steps may also be included without departing from the principles of this invention. While these additives and steps expressly cover all foreseeable equivalents of the elements recited above, additional variations are possible. For example, it is possible to include a coloring agent and or olfactory substances to enhance the aesthetics or apparent authenticity of the synthetic urine produced according to this invention.

The foregoing detailed description has been given for clearness of understanding only and no unnecessary limitations should be understood therefrom as some modifications will be obvious to those skilled in the art without departing from the scope and spirit of the appended claims.

I claim:

1. A synthetic urine solution comprising:
   water having a pH between 3 and 10;
   creatinine and a biocide, said creatinine and biocide dissolved within said water to form a solution exhibiting a specific gravity and said creatinine and biocide selected in relative concentrations to minimize sepsis;
   at least one dissociated ionic compound also dissolved within said solution to adjust the specific gravity of the solution to between 1.005 $g/cm^3$ and 1.025 $g/cm^3$; and
   wherein said biocide is selected from the group consisting of 2-bromo-4-hydroxyacetophenone, bronopols, carbamates, chlorothioethers, 2-2-Dibromo-3-nitrilopropionamide, 2-(Decylthio)ethanamine, glutaraldehydes, isothiazolines, Methylene bis(thiocyanate), polyquat, Alkyldimethylbenzylammonium chloride, sulfones, Bis(tributyltin) oxide, tertbuthylazines, Tetrachloro-2,4,6-cyano-3-benzonitrile, 2(thiocyanomethylthio)benzothiazole, thiones, Tetrakish(hydroxymethyl)phosphonium sulfate, Tributyltetradecylphosphonium chloride, peroxides, hypochlorites, and super oxides.

2. The synthetic urine solution of claim 1, further including urea dissolved within said solution.

3. The synthetic urine solution of claim 1, wherein said at least one ionic compound is selected from the group consisting of carbonate salts, halide salts, hydroxide salts and bromides.

4. The synthetic urine solution of claim 3, further including urea dissolved within said solution.

5. A method of manufacturing a synthetic urine solution comprising:
   providing water;
   dissolving creatinine and biocide into said water to form a solution exhibiting a specific gravity level, said creatinine and biocide being selected in relative concentrations to minimize sepsis, wherein said biocide is selected from the group consisting of 2-bromo-4-hydroxyacetophenone, bronopols, carbamates, chlorothioethers, 2-2-Dibromo-3-nitrilopropionamide, 2-(Decylthio)ethanamine, glutaraldehydes, isothiazolines, Methylene bis(thiocyanate), polyquat, Alkyldimethvlbenzylammonium chloride, sulfones, Bis(tributyltin) oxide, tertbuthylazines, Tetrachloro-2, 4,6-cyano-3-benzonitrile, 2(thiocyanomethylthio) benzothiazole, thiones, Tetrakish(hydroxymethyl) phosphonium sulfate, Tributyltetradecylphosphonium chloride, peroxides, hypochlorites, and super oxides; and adjusting said specific gravity level of said solution to between 1.005 g/cm$^3$ and 1.025 g/cm$^3$.

6. The method of claim 5 further comprising sealing said synthetic urine solution within a container so as to further minimize sepsis of said synthetic urine solution.

7. The method of claim 6 further comprising adding urea to said synthetic urine solution.

8. The method of claim 5 further comprising adding urea to said synthetic urine solution.

9. The method of claim 5, further comprising the step of adjusting the pH level of the solution between 3 and 10.

10. A method of manufacturing a synthetic urine solution comprising:

providing water having a pH between 3 and 10;

dissolving creatinine and at least one dissociating ionic compound in the water to form a solution exhibiting a specific gravity, said creatinine and at least one dissociating ionic compound selected in relative concentrations to adjust said specific gravity to between 1.005 g/cm$^3$ and 1.025 g/cm$^3$; adding a biocide into said solution, said biocide is selected from the group consisting of 2-bromo-4-hydroxyacetophenone, bronopols, carbamates, chlorothioethers, 2-2-Dibromo-3-nitrilopropionamide, 2-(Decylthio)ethanamine, glutaraldehydes, isothiazolines, Methylene bis(thiocyanate), polyquat, Alkyldimethylbenzylamnionium chloride, sulfones, Bis(tributyltin) oxide, tertbuthylazines, Tetrachloro-2, 4,6-cyano-3-benzonitrile, 2(thiocyanomethylthio)benzothiazole, thiones, Tetrakish(hydroxymethyl)phosphonium sulfate, Tributyltetradecylphosphonium chloride, peroxides, hypochlorites, and super oxides; and removing bacteria from said solution.

11. The method of claim 10 wherein the step of dissolving creatinine and at least one dissociating ionic compound also includes dissolving urea in the water, said urea selected in a concentration relative to that of said creatinine and at least one dissociating ionic compound so as to maintain the specific gravity of the solution between 1.005 g/cm$^3$ and 1.025 g/cm$^3$.

12. The method of claim 11, further comprising the step of sealing said synthetic urine solution within a container.

13. The method of claim 10, further comprising the step of sealing said synthetic urine solution within a container.

* * * * *